United States Patent
Wu et al.

(10) Patent No.: US 8,891,824 B2
(45) Date of Patent: Nov. 18, 2014

(54) METHOD AND DEVICE FOR DETECTING FATIGUE DRIVING AND THE AUTOMOBILE USING THE SAME

(75) Inventors: Zejun Wu, Shenzhen (CN); Ruzhong Cheng, Shenzhen (CN); Wei Chen, Shenzhen (CN); Yong Dai, Shenzhen (CN); Yong Zhao, Shenzhen (CN); Yunli Qing, Shenzhen (CN)

(73) Assignee: Shenzhen Safdao Technology Corporation, Guangdong (CN)

( * ) Notice: Subject to any disclaimer, the term of this patent is extended or adjusted under 35 U.S.C. 154(b) by 392 days.

(21) Appl. No.: 13/504,762

(22) PCT Filed: Oct. 28, 2010

(86) PCT No.: PCT/CN2010/078199
§ 371 (c)(1),
(2), (4) Date: Apr. 27, 2012

(87) PCT Pub. No.: WO2011/050734
PCT Pub. Date: May 5, 2011

(65) Prior Publication Data
US 2012/0219189 A1      Aug. 30, 2012

(30) Foreign Application Priority Data
Oct. 30, 2009   (CN) .......................... 2009 1 0110369

(51) Int. Cl.
*G06K 9/00*       (2006.01)
*A61B 5/18*       (2006.01)
*A61B 5/11*       (2006.01)
*A61B 5/00*       (2006.01)

(52) U.S. Cl.
CPC .................. *A61B 5/18* (2013.01); *A61B 5/1103* (2013.01); *G06K 9/00597* (2013.01); *G06K 9/00845* (2013.01); *A61B 5/6821* (2013.01); *A61B 2503/22* (2013.01)
USPC .......................................................... 382/103

(58) Field of Classification Search
CPC .................................................. G06K 9/00845
See application file for complete search history.

(56) References Cited

U.S. PATENT DOCUMENTS 7,253,738 B2      8/2007   Hammoud et al.

FOREIGN PATENT DOCUMENTS

| CN | 101375796 A | 3/2009 |
|---|---|---|
| CN | 101523411 A | 9/2009 |
| CN | 10169280 A | 4/2010 |
| JP | 2000102510 | 4/2000 |

OTHER PUBLICATIONS

International Search Report in corresponding PCT Application No. PCT/CN1010/078199, dated Jan. 20, 2011.

*Primary Examiner* — Atiba O Fitzpatrick
(74) *Attorney, Agent, or Firm* — Dicke, Billig & Czaja, PLLC (57) ABSTRACT

The present application discloses a method and device of detecting fatigue driving, comprising: analyzing an eye image in the driver's eye image area with a rectangular feature template to obtain the upper eyelid line; determining the eye closure state according to the curvature or curvature feature value of the upper eyelid line; and collecting statistics on the eye closure state and thereby determining whether the driver is in a fatigue state. The present application determines whether the eyes are opened or closed according to the shape of the upper eyelid, which is more accurate because the upper eyelid line has characteristics of higher relative contrast, anti-interference capacity, and adaptability to the changes in the facial expression.

20 Claims, 7 Drawing Sheets

METHOD AND DEVICE FOR DETECTING FATIGUE DRIVING AND THE AUTOMOBILE USING THE SAME

TECHNICAL FIELD

The present application relates to the safe vehicle-driving technology, and particularly to the fatigue-driving monitoring technology.

PRIOR ART

The aim of the advanced automobile safety technology is the active safety technology; that is, by monitoring the driver and vehicle as well as the surrounding environment, judging the possible risks in advance and taking preventive measures. The driver fatigue early-warning technology is exactly a typical active safety technology. When a driver is in a fatigue state, he is weakened in various degrees in the abilities of perceiving and judging the surrounding environment and handling the vehicle, and thus prone to traffic accidents. Therefore, research and development of the high-performance real-time monitoring and early-warning technology for a driver's attention can effectively reduce the hidden dangers resulted from such behaviors as fatigue driving, so as to achieve the purpose of ensuring the safety of the driver and the surrounding related personnel.

The fatigue-driving early-warning technology taking the driver's eyes as a detected object determines the inattention degree mainly by detecting the driver's eye state, which generally uses a camera for collecting the images of the driver's face and eye, and then determines the eye state by image analysis and modeling. A key technology related is determining the open/closed state of the driver's eyes.

Most of the current fatigue-monitoring methods determine whether a driver's eyes are closed by determining the eye state, which has the following major problems:

1. Slow processing speed. A lot of processing needs to be performed on the images, and the analysis method is complicated and cannot meet the real-time requirements, usually one second only enough for processing several frames of image. In the driving process, however, if the driver's eyes are closed or nearly closed for one second or so, according to different speeds of the automobile, the driver may not observe the road situation ahead and then may cause a major safety accident. Only when the real-time requirements are met, can the data accuracy be guaranteed and the determination accuracy be improved.

2. Poor adaptability. First, the eye state can be accurately determined with an image of good quality; however, once the image is unclear and the number of noisy points increases under the influence of such factors as dark light, definition of the camera and movement of the driver's head, the accuracy cannot be guaranteed. Second, when the driver moves back and forth or left and right to cause the eye image to change in size and angle, the dynamic adaptation cannot be achieved, making the accuracy fluctuate.

Due to the above various defects, many of the methods, once leaving the laboratory environment for actual use in an automobile, are hard to achieve desired effects and thus have no practicality.

SUMMARY

The present application provides a method and device for detecting fatigue driving that can increase the overall processing speed and have strong adaptability.

On one hand, the present application provides a method for detecting fatigue driving comprising:

analyzing a driver's eye image with a rectangular feature template to obtain an upper eyelid line, in particular, traversing the eye image by columns with the rectangular feature template and recording the location in each column where the feature value of the rectangular feature template is maximal, the feature value of the rectangular feature template referring to a greyscale difference between the upper and lower halves of the rectangle where the rectangular feature template is located, and obtaining the upper eyelid line by taking the central point of the rectangular feature template at the location as a point on the upper eyelid line;

determining the eye closure state according to a curvature or curvature feature value of the upper eyelid line; and collecting statistics on the eye closure state and thereby determining whether the driver is in a fatigue state.

On another hand, the present application provides a fatigue-driving detecting device comprising: an upper-eyelid-line acquiring module for scanning a driver's eye image with a rectangular feature template to obtain an upper eyelid line; a first determining module for determining the eye closure state according to a curvature or curvature feature value of the upper eyelid line; and a fatigue-state determining module for collecting statistics on the eye closure state and thereby determining whether the driver is in a fatigue state.

The upper-eyelid-line acquiring module comprises: a scanning unit for sliding the rectangular feature template on each column of the eye image; a greyscale-difference calculating unit for recording the location in each column where the feature value of the rectangular feature template is maximal, the feture value of the rectangular feature template referring to a greyscale difference between the upper and lower halves of the rectangle where the rectangular feature template is located; and an upper-eyelid-line plotting unit for taking the central point of the rectangular feature template at the location as a point on the upper eyelid line.

In an example, the fatigue-driving detecting device further includes a fitting module used for performing curve fitting on the eyelid line with a quadratic polynomial to get a quadratic polynomial expression of the eyelid line, regarding a quadratic coefficient of the quadratic polynomial expression as the curvature or curvature feature value of the upper eyelid line; the first determining module is used for comparing the quadratic coefficient with a preset eyelid-line curvature threshold, and thereby determining whether the driver's eyes are opened or closed.

In another example, the eyelid-line curvature threshold includes a first threshold and a second threshold less than the second threshold; when the quadratic coefficient is greater than the first threshold, the driver's eyes are determined by the first determining module to be in an opened state; when the quadratic coefficient is less than the second threshold, the driver's eyes are determined by the first determining module to be in a closed state; when the quadratic coefficient is between the first and second thresholds, a second determining module is further included for an auxiliary determination of the eye closure state according to a spacing between the upper and lower eyelids.

In an example, the fatigue-driving detecting device further includes a lower-eyelid-line acquiring module for scanning the eye image with the rectangular feature template based on the acquired upper eyelid line to obtain the lower eyelid line. The second determining module includes: an upper-and-lower eyelid line spacing computing unit for computing the average spacing between the upper and lower eyelid lines; and a spacing comparing unit for comparing the average spacing between the upper and lower eyelid lines with the preset eyelid-line spacing threshold and thereby determining whether the driver's eyes are opened or closed.

In an example, the eyelid-line spacing threshold changes dynamically with the curvature or curvature feature value of the upper eyelid line; when the average spacing between the upper and lower eyelid lines is greater than the eyelid-line spacing threshold, the driver's eyes are determined to be in an opened state, otherwise to be in a closed state.

In an example, the upper-eyelid-line acquiring module further includes an integrating unit used for integrating the eye image before traversing the eye image to obtain the integral eye image; the upper-eyelid-line acquiring module is configured for scanning the integral eye image with the rectangular feature template, computing the feature value of the rectangular feature template at each location, the value of each point in the integral eye image being equal to the sum of greyscale of the rectangular area in the eye image with the origin and this point as the diagonal points, the sum of greyscale of one rectangle being equal to the value at the upper left corner of the rectangle plus the value at the lower right corner minus the value at the lower left corner minus the value at the upper right corner.

In another example, the fatigue-driving detecting device further includes a denoising module used for denoising the obtained upper eyelid line, the denoising module including: an eyelid-line dividing unit for detecting discontinuous points on the eyelid line, and dividing the eyelid line into several sections by taking the discontinuous points as segmentation points; a trust-section determining unit for determining the trust section on the eyelid line as a basis of the eyelid line; and an eyelid-line correcting unit for scanning locally with the rectangular feature template from both ends of the trust section respectively toward both sides to obtain a corrected eyelid line.

On yet another hand, the present application provides an automobile comprising: a camera device, fixed near the driver's position for taking the driver's face image; and the fatigue-driving detecting device as described above, arranged on the automobile for receiving and processing image data from the camera device.

The present application further discloses a computer executable program that can perform the following functions by a computer:

analyzing a driver's eye image with a rectangular feature template to obtain an upper eyelid line, in particular, traversing the eye image by columns with the rectangular feature template and recording the location in each column where the feature value of the rectangular feature template is maximal, the feature value of the rectangular feature template referring to a greyscale difference between the upper and lower halves of the rectangle where the rectangular feature template is located, and obtaining the upper eyelid line by taking the central point of the rectangular feature template at the location as a point on the upper eyelid line;

determining the eye closure state according to the curvature or curvature feature value of the upper eyelid line; and collecting statistics on the eye closure state and thereby determining whether the driver is in the fatigue state.

The present application further discloses a computer readable medium with the above computer executable program recorded thereon, which can perform the following functions by a computer:

analyzing a driver's eye image area with a rectangular characteristic template to obtain an upper eyelid line, in particular, traversing the eye image by columns with the rectangular feature template and recording the location in each column where the feature value of the rectangular characteristic template is maximal, the feature value of the rectangular feature template referring to a greyscale difference between the upper and lower halves of the rectangle where the rectangular feature template is located, and obtaining the upper eyelid line by taking the central point of the rectangular feature template at the location as a point on the upper eyelid line;

determining the eye closure state according to a curvature or curvature feature value of the upper eyelid line; and collecting statistics on the eye closure state and thereby determining whether the driver is in a fatigue state.

The present application, using the rectangular feature template to scan and search the eye area and plot the eyelid line, has good anti-interference capacity; by combining the rectangular templates of different sizes, an eyelid line more coinciding with the actual eyelid line can be plotted during denoising. The present application, needing no complicated and time-consuming processing of the image, has high overall running speed and efficiency. The present application, determining whether the eyes are opened or closed according to the shape of the upper eyelid, is more accurate because the upper eyelid line has a higher relative contrast, anti-interference capacity, and adaptability to the changes in the facial expression.

DETAILED DESCRIPTION

The application will further be described below in detail in combination with embodiments and drawings.

Example 1

Figure 1:
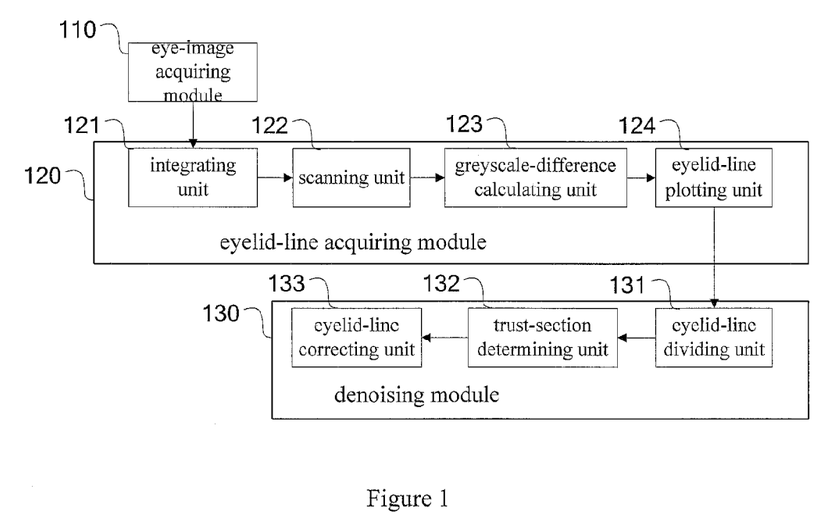
FIG. 1 is a schematic view of the structure of the eyelid-line detecting device according to an example of the application.

As shown in FIG. 1, in an example according to the application, the line corresponding to eyelid, i.e., eyelid line, is detected with a rectangular feature template. The eyelid-line detecting device includes an eye-image acquiring module 110 and an eyelid-line acquiring module 120. The eye-image acquiring module 110 is used for acquiring a driver's eye image; and the eyelid-line acquiring module 120 is used for scanning the driver's eye image with a rectangular feature template to obtain an eyelid line. In an example, the eyelid-line acquiring module 120 can further include a scanning unit 122, a greyscale-difference calculating unit 123 and an eyelid-line plotting unit 124. The scanning unit 122 is used for scanning by columns the driver's eye image with a rectangular feature template; the greyscale-difference calculating unit 123 is used for recording the location in each column where the feature value of the rectangular feature template is maximal, the feature value of the rectangular feature template referring to a greyscale difference between the upper and lower halves of the rectangle where the rectangular feature template is located; the eyelid-line plotting unit 124 is used for obtaining the eyelid line by taking the central point of the rectangular feature template at the location as a point on the eyelid line.

In another example, the eyelid-line acquiring module 120 further includes an integrating unit 121 for integrating the eye image to obtain an integral eye image; the scanning unit 122 scans the integral eye image with a rectangular feature template, the greyscale value of each point in the integral eye image being equal to the sum of the greyscale of the rectangular area in the eye image with the origin and this point as the diagonal points.

In yet another example, the eyelid-line detecting device further includes a denoising module 130 used for denoising the obtained eyelid line, the denoising module 130 including: an eyelid-line dividing unit 131, a trust-section determining unit 132 and an eyelid-line correcting unit 133. The eyelid-line dividing unit 131 is used for detecting discontinuous points on the eyelid line, and dividing the eyelid line into several sections by taking the discontinuous points as segmentation points; the trust-section determining unit 132 is used for determining a trust section in the eyelid line as a basis of the eyelid line; and the eyelid-line correcting unit 133 is used for scanning with a rectangular feature template from both ends of the trust section respectively toward both sides to obtain a corrected eyelid line.

Example 2

Figure 2:
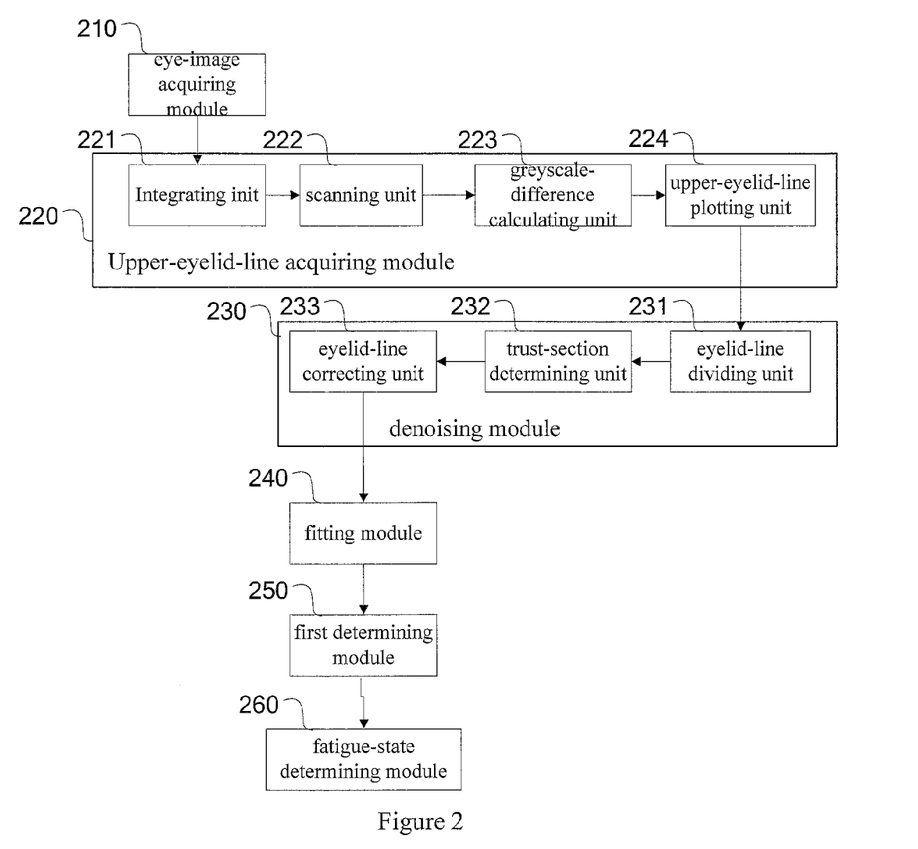
FIG. 2 is a schematic view of the structure of the fatigue-driving detecting device according to an example of the application.

As shown in FIG. 2, the example shown in FIG. 2 is the application of the above eyelid-line detecting device in a fatigue-driving detecting device, the fatigue-driving detecting device including: an eye-image acquiring module 210, an upper-eyelid-line acquiring module 220, a first determining module 250 and a fatigue-state determining module 260. The eye-image acquiring module 210 is used for obtaining the driver's eye image according to the device's face image taken by a camera device (e.g. a camera); the upper-eyelid-line acquiring module 220 is used for scanning the driver's eye image with a rectangular feature template to obtain the line corresponding to the upper eyelid, i.e., upper eyelid line; the first determining module 250 is used for determining the state of eye closure according to a curvature or curvature feature value of the upper eyelid line; and the fatigue-state determining module 260 is used for collecting statistics on the state of eye closure and thereby determining whether the driver is in a fatigue state.

The upper-eyelid-line acquiring module 220 includes: an integrating unit 221, a scanning unit 222, a greyscale-difference calculating unit 223 and an upper-eyelid-line plotting unit 224. The integrating unit 221 is used for integrating the eye image to obtain an integral eye image; the scanning unit 222 is used for scanning the integral eye image with a rectangular feature template, specifically sliding on each column of the integral image to calculate the greyscale value of each point. In the integral eye image, the greyscale value of each point is equal to the sum of greyscale of the rectangular area in the eye image with the origin and this point as the diagonal points. The greyscale-difference calculating unit 223 is used for recording the location in each column where the feature value of the rectangular feature template is maximal, the feature value of the rectangular feature template referring to the greyscale difference between the upper and lower halves of the rectangle where the rectangular feature template is located; the upper-eyelid-line plotting unit 224 is used for taking the central point of the rectangular feature template at the location as a point on the upper eyelid line, and in this way scanning and computing each column in the integral image to plot the eyelid line.

In an example, because the preliminarily obtained eyelid line is to be further corrected after the acquisition thereof, the fatigue-driving detecting device further includes a denoising module 230 for removing some interference points or interference line segments on the preliminary eyelid line. The denoising module 230 includes: an eyelid-line dividing unit 231, a trust-section determining unit 232 and an eyelid-line correcting unit 233. The eyelid-line dividing unit 231 is used for detecting discontinuous points on the eyelid line, and dividing the eyelid line into several sections by taking the discontinuous points as segmentation points; the trust-section determining unit 232 is used for determining a trust section in the eyelid line as the basis of the eyelid line; and the eyelid-line correcting unit 233 is used for scanning with the rectangular feature template from both ends of the trust section respectively toward both sides to obtain a corrected eyelid line.

In another example, the curvature or curvature characterization value of the upper eyelid line is acquired through a fitting module 240, which performs curve fitting on the eyelid line with a quadratic polynomial to get a quadratic polynomial expression of the eyelid line, with the quadratic coefficient of the quadratic polynomial expression as the curvature or curvature characterization value of the upper eyelid line; the first determining module 250 is used for comparing the quadratic coefficient with a preset eyelid-line curvature threshold, and thereby determining whether the driver's eyes are opened or closed.

Figure 3:
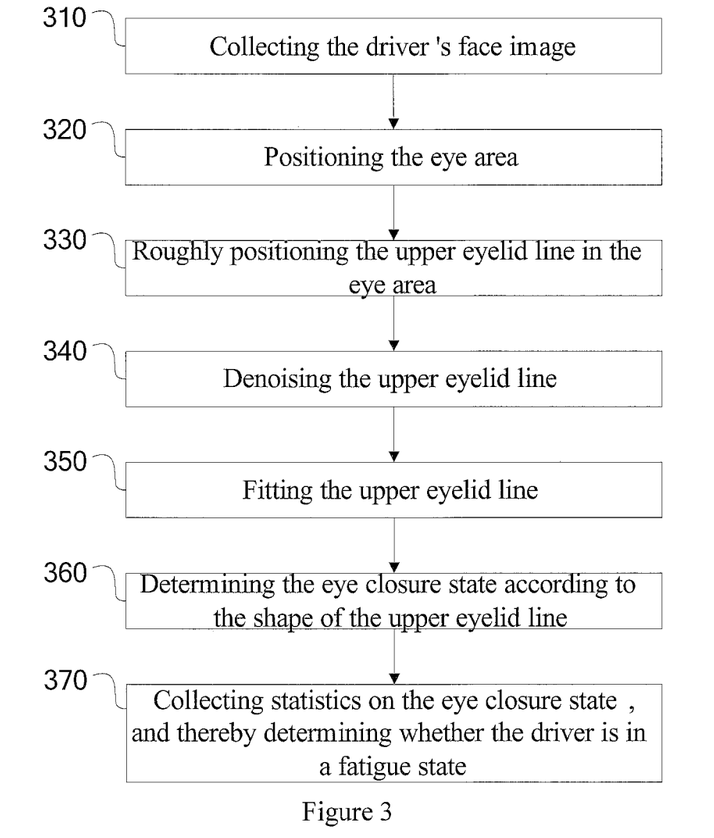
FIG. 3 is a flow chart of the method for detecting fatigue driving according to an example of the application.

As shown in FIG. 3, the method of detecting fatigue driving with the above-mentioned fatigue-driving detecting device includes the following steps:

Step 310, collecting the driver's face image. For example, taking the driver's face image with an infrared camera installed in front of or in lower front of the driver to get the driver's face image data, and then going to Step 320.

Step 320, positioning the eyebrow and eye areas in the face image. Various existing solutions of positioning the eyebrow and eye areas can be used, and this example only describes a method of detecting eyes with an example. For example, positioning the face region according to a pre-trained facial feature classifier. After reading each frame of the video image, analyzing the face image information according to the Harr features recorded in the facial feature classifier, and performing pattern recognition on the image with the AdaBoost algorithm and related facial feature classifier to calibrate the face region in the image. Then determining the region of interest for the eye detection in the face region according to the basic position where the driver's eyes are located, e.g. the middle of the face area, to narrow the detection range of the eyes and increase the detection speed. And then analyzing the image of the region of interest for the eye detection according to the eye features recorded in the pre-trained eye feature classifier to position the eye area. Going to Step 330 after positioning the eye area.

Figure 4:
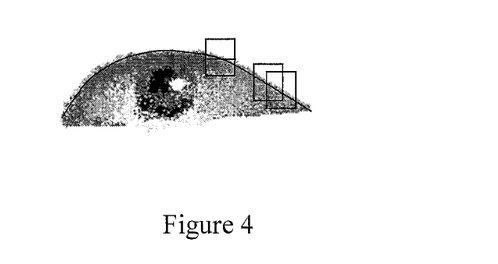
FIG. 4 is a schematic view of roughly-positioning the upper eyelid line.

Step 330, roughly positioning the upper eyelid line in the eye area. Scanning the eye image with a rectangular feature template, traversing each column of the eye image, and analyzing the greyscale variation of the eye image, thus obtaining the upper eyelid line. The rectangular feature template is a rectangular window, which is used to slide on each column of the eye image, as shown in FIG. 4; calculating the greyscale difference between the upper and lower halves of the rectangle of the rectangular feature template (the box in the drawing) at each location in the sliding process, and recording the location of the biggest feature value by defining the greyscale difference to be the feature value of the rectangular feature template, with the central point of the rectangular feature template at the location as a point on the upper eyelid line. Traversing each column successively, with one point on each column recorded as a point on the upper eyelid line, all the points together yielding the plotted eyelid line.

In an example, in order to increase the operational speed, integrating the eye image after roughly positioning the eye image to obtain the integral eye image, with the value of a point P in the integral image be the sum of greyscale of the rectangular area in the greyscale image with the origin of the image and the point P as the diagonal points. The integral image S of the greyscale image I is defined as follows:

$$S(u,v) = \int_{x=0}^{u} \int_{y=0}^{v} I(x,y) dx dy$$

Figure 5:
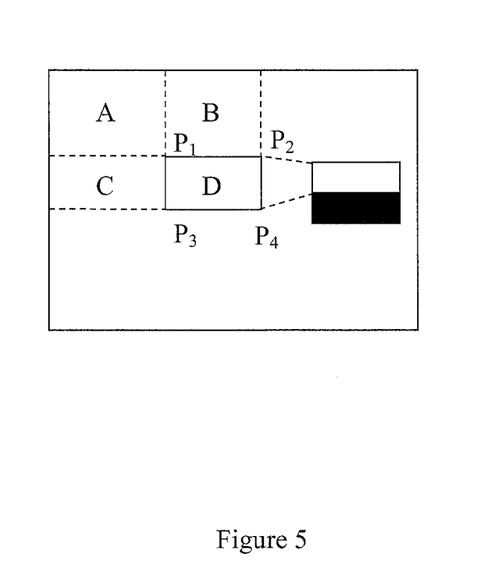
FIG. 5 is a schematic view of calculating the feature value of the template with the integral image.

The greyscale difference between the upper and lower parts of the rectangular characteristic template is calculated as shown in FIG. 5. The value of the point P1 means the sum of greyscale of the area A, and is simply recorded as A; the value of the point P2 is A+B; the value of the point P3 is A+C; and the value of the point P4 is A+B+C+D. Hence, the sum of greyscale of the rectangular area D enclosed by P1, P2, P3 and P4 can be represented as P1+P4−P2−P3. The calculation of gray feature of the rectangular template with the help of the integral image is irrelevant to the size of the rectangle.

Calculation of the integral image only needs to traverse the image once and record the greyscale value of each point rather than to calculate once for each traversing, thus making the calculation speed very quick by calculating the characteristic value with the integral image.

For further increasing the accuracy, matching can be performed many times on the upper eyelid from roughness to preciseness. First using a larger rectangular template to search for the eyelid line, and then scanning with a smaller rectangular template near the acquired eyelid line, with the operation in this way for many times. The larger rectangular template has better anti-interference capacity, while the smaller rectangular template can better coincide with the actual edge.

The size of the rectangular template can be either specified statically or determined dynamically according to the size of the image, with the latter having better adaptability.

Figure 6:
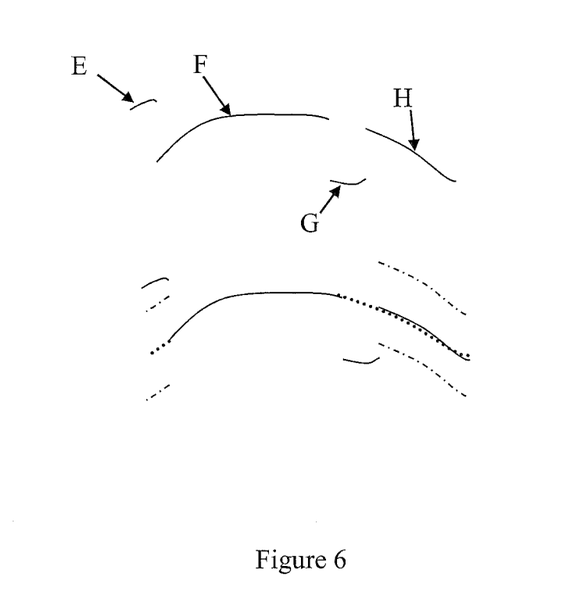
FIG. 6 is a schematic view of correcting the upper eyelid line.

After preliminarily plotting the upper eyelid line, in order to make the plotted eyelid line more coincide with the actual eyelid line, denoising the preliminarily plotted upper eyelid line in Step 340 to remove the incredible points or sections on the eyelid line. The denoising process includes the following steps:

1. Detecting discontinuous points on the eyelid line, and dividing the eyelid line into several sections by taking the discontinuous points as segmentation points. Calculating the distance difference lengthways between the front and rear points to find out the points having a distance difference greater than a specific threshold, and dividing the upper eyelid line into several sections as shown in FIG. 6, where the entire eyelid line can be divided into four sections of E, F, G and H. The threshold Df can be calculated with the following formula, where L is the length of the upper eyelid line and n an empirical value.

$$D_f = L/n$$

2. Determining a trust section on the eyelid line as a basis of the eyelid line.

3. Scanning with the rectangular feature template from both ends of the trust section respectively toward both sides to obtain the corrected eyelid line.

Scanning with the rectangular feature template leftward and rightward from both ends of the trust section to extend the section, where the scanned range is a scope within certain upper and lower thresholds taking the coordinate Y of the starting point as a center; the thresholds can be adjusted according to the size of the image and be smaller than the distance difference when searching for the discontinuous points. For example, the right end of the longest section has an X value of 30 and a Y value of 20 as well as a threshold value of 5, and then the scanned range of the next point is between Line 31 and Lines 15-25. Then searching for the next point based on the new right end, and so forth. As shown in FIG. 6, the solid line is the preliminarily detected eyelid line, and the dotted lines at both ends of the solid line are the eyelid line extended by way of scanning with the rectangular feature template, the case being similar for the left side.

There are the following two cases while determining the trust section:

1. Finding out the section having a length greater than ½L in the several divided sections, and taking this section as the trust section; and then extending this section toward both sides by the method in Step 3.

2. If the trust section is not found according to the case 1, finding out all the sections having a length greater than ¼L, and processing them according to the number of the sections meeting the conditions, respectively.

If there is only one section having a length greater than ¼L, finding out the longest section in the rest of the sections, and processing them according to two sections.

If there are two sections meeting the conditions, extending one of them toward the other section in a similar way to Step 3 and, if the extended on is overlapped with the other section, forming a new section composed of the two sections and all the points obtained in the extending process between the two sections. Taking the new section as the trust section, and extending it toward both sides by the method in Step 3. Another method is as follows: First extending one of the sections leftward and rightward, respectively to connect the next section separated by one section; if the connection can be done, continuing to extend from both ends of the new section formed by the connection, until there is no section to be connected or able to be connected in either of the two directions. Recording the starting position of the new section. Recovering the initial data of each section. Extending the other section in the same way. Comparing the lengths of the new sections after extension of the two sections, taking the longest new section obtained by the extension (the initial section) as the trust section, and extending it toward both sides by the method in Step 3.

If there are three sections having a length bigger than ¼L, extending the middle section toward both sides in a similar way to Step 3 to connect the left or right section. If the connection can be done, taking the new section as the trust section. Or connecting the central section to the section at one side. If the connection can be done, taking the new section as the trust section; if the connection cannot be done, connecting the left and right sections, and taking the new section thus formed as the trust section. After forming the trust section, extending it toward both sides by the method in Step 3.

Going to Step 350 after denoising the eyelid line, and fitting the upper eyelid line. Performing the least square fitting with a quadratic polynomial expression $y=ax^2+bx+c$ as the fitting function. Because the intercepted image may include a part besides the two canthi that usually has a smaller greyscale difference, in order to further eliminate the interference of this part to the results, removing the points while fitting that have the corresponding rectangular-template greyscale difference smaller than a certain threshold, such as taking twice the area of the template as the threshold.

Obtaining a quadratic polynomial expression of the eyelid line after fitting, taking the quadratic coefficient a of the quadratic polynomial expression as the curvature or curvature feature value of the upper eyelid line, and then going to Step 360.

Step 360, determining the state of eye closure i.e. the eye closure state according to the curvature or curvature feature value of the upper eyelid line, which specifically includes: comparing the quadratic coefficient a with a preset eyelid-line curvature threshold; and thereby determining whether the driver's eyes are opened or closed.

Step 370, collecting statistics on the eye closure state, and thereby determining whether the driver is in a fatigue state. For example, collecting statistics on a duration when the eyes are closed in a recent time, and determining that the driver is in the fatigue state if the eye closed duration exceeds a specified duration; or collecting statistics on a ratio of eye open duration to eye closed duration in unit time, and determining that the driver is in the fatigue state if the ratio in unit time exceeds a certain threshold.

This example acquires the eyelid line by the method of column-by-column matching with a rectangular feature template, which does not need to perform excessive processing on the images, thus making the example has advantages of fast overall speed, good adaptability to the degradation of image quality resulted from such various conditions as light, and good adaptability to the driver's back-and-forth movement.

This example determines the driver's eye closure state according to the curvature of the eyelid, and since the upper eyelid line has characteristics of higher relative contrast, anti-interference capacity and adaptability to the changes in the facial expression, such as the radian of the upper eyelid usually changes little while the driver smiles or squints, this example makes a more accurate determination compared with the method of determining the eye closure state according to the spacing between the upper and lower edges of the iris or the upper and lower eyelids, reduces the influence of the driver's head pose on the determination, and increases the accuracy of fatigue determination. Besides, this example has good overall system timeliness and high sensitivity, and can effectively reduce false and missed reports and has better practicability.

This example, before scanning, firstly computes the integral eye image, which consumedly increasing the speed of calculation of the feature value of the rectangular feature template.

Different from other denoising algorithms based on the estimated value correction, this example takes the longer section as the trusted section, and corrects the eyelid line based on the measured values by scanning with the rectangular feature template within the local range at both ends of the trust section, which is thus more accurate.

This example, the acquired eyelid line is smoothed by the least square method, which eliminates the phenomenon that the acquired eyelid line is not so smooth due to a poor image quality, making the eyelid line more coincide with the actual eyelid shape; this example further eliminates the interference of individual noisy points at the same time. Because the upper eyelid line is respectively close to a parabola and a straight line when the eyes are opened and closed, this example takes the quadratic polynomial expression $y=ax^2+bx+c$ as the fitting function. After processed by the least square method, the quadratic polynomial expression of the eyelid line can be obtained; the quadratic coefficient of the quadratic polynomial can better reflect the curvature of the upper eyelid and, is more accurate compared with other methods of directly calculating the curvature, having a better adaptability to the image angle and quality.

Example 3

This example further increases the accuracy of determining the eye closure state. Because some persons have the upper eyelids with an unobvious radian due to such reasons as even upper eyelids or looking down, the curvature of the upper eyelid does not change obviously when the eyes are opened and closed; if determining the driver's eye closure state simply according to the curvature of the upper eyelid, sometimes an erroneous determination may be made. In this example, besides determining the driver's eye closure state according to the curvature of the upper eyelid, the average spacing between the upper and lower eyelids is further used for auxiliary determination.

Figure 7:
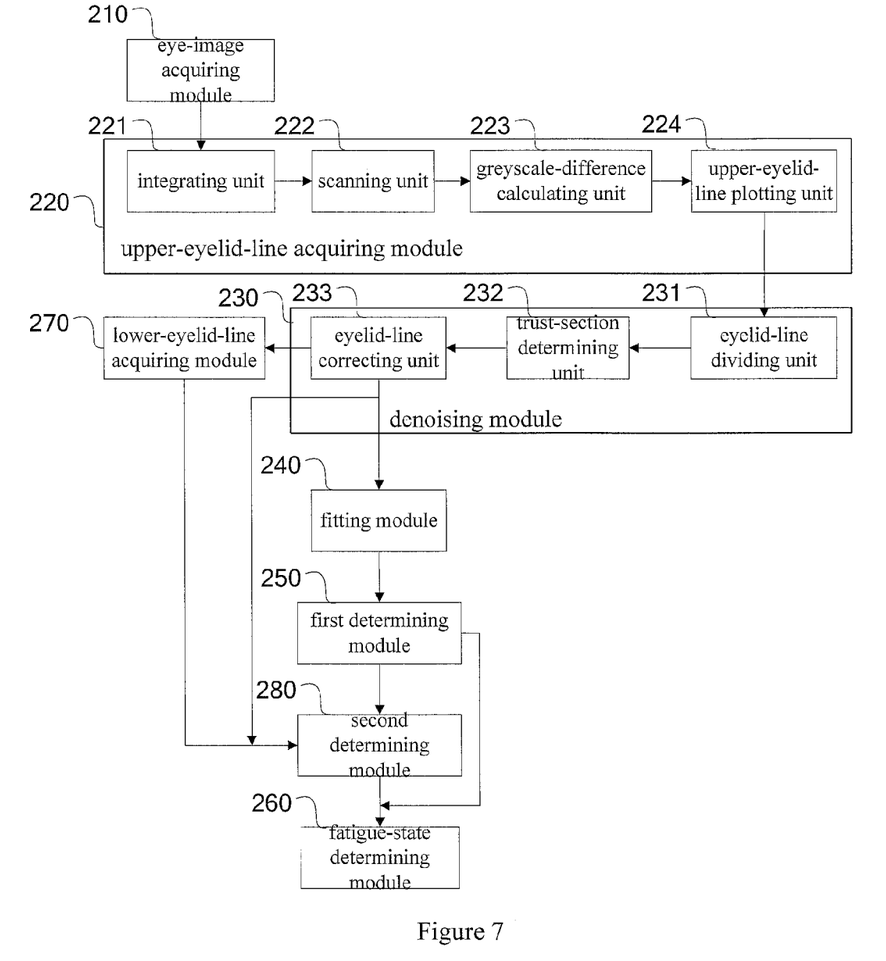
FIG. 7 is a schematic view of the structure of the fatigue-driving detecting device according to another example of the application.

A schematic view of the structure of the fatigue-driving detecting device of this example is as shown in FIG. 7, a second determining module 280 and a lower-eyelid-line acquiring module 270 being added in the above example. The lower-eyelid-line acquiring module 270 is used for obtaining the line corresponding to the lower eyelid i.e. lower eyelid line based on the acquired upper eyelid line by scanning the eye image with the rectangular feature template.

The second determining module 280, after the preliminary determination by the first determining module 250, makes another auxiliary determination on the eye closure state according to the average spacing between the upper and lower eyelids.

In an example, the eyelid-line curvature threshold includes a first threshold and a second threshold less than the first threshold; when the quadratic coefficient is greater than the first threshold, the driver's eyes are determined by the first determining module to be opened; when the quadratic coefficient is smaller than the second threshold, the driver's eyes are determined to be closed; when the quadratic coefficient is between the first and second thresholds, an auxiliary determination is made by the second determining module on the eye closure state according to the spacing between the upper and lower eyelids.

The second determining module 280 includes an upper-and-lower eyelid line spacing computing unit and a spacing comparing unit. The upper-and-lower eyelid line spacing computing unit calculates the average spacing between the upper and lower eyelid lines according to the plotted upper and lower eyelid lines; and the spacing comparing unit is used for comparing the average spacing between the upper and lower eyelid lines with a preset eyelid-line spacing threshold and thereby determining whether the driver's eyes are opened or closed.

In an example, the eyelid-line spacing threshold can be changed dynamically with the curvature or curvature feature value of the upper eyelid line; when the average spacing between the upper and lower eyelid lines is greater than the eyelid-line spacing threshold, the driver's eyes are determined to be opened, otherwise to be closed.

Figure 8:
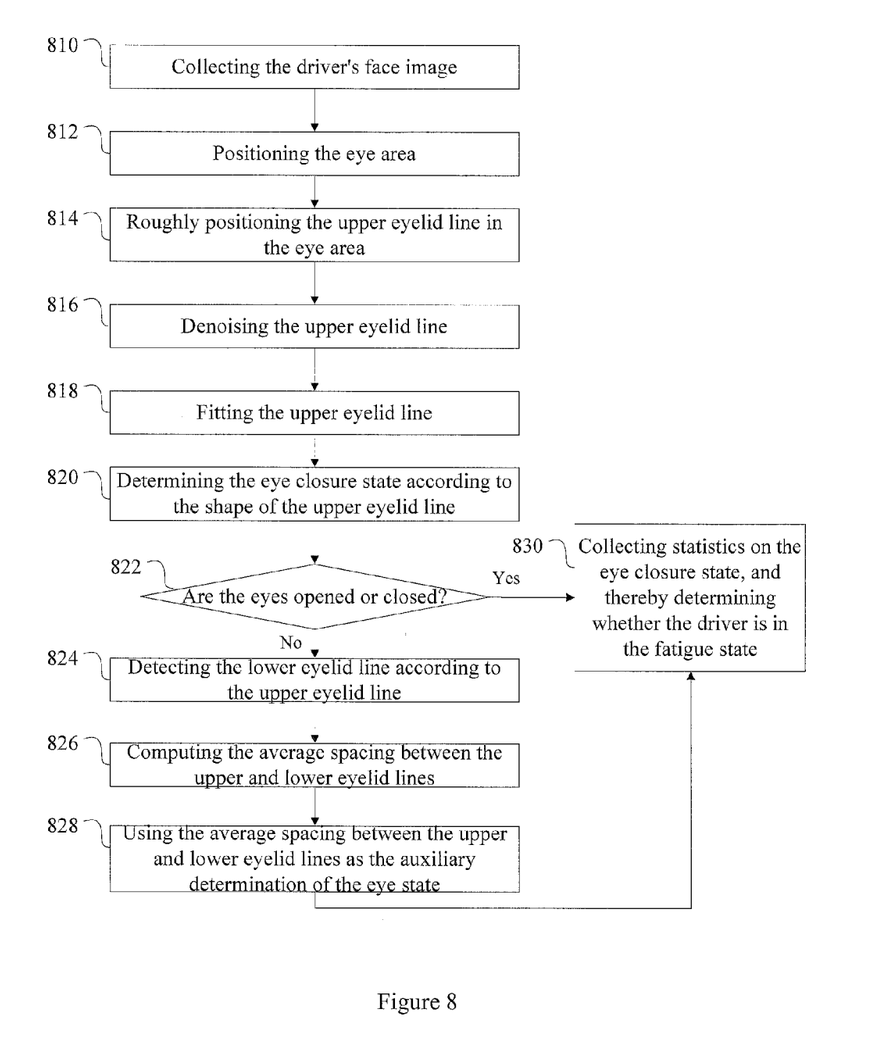
FIG. 8 is a flow chart of the method of detecting fatigue driving according to another example of the application.

An method for detecting fatigue driving based on the fatigue-driving detecting device of this example is as shown in FIG. 8, including the following steps:

Step 810, collecting the driver's face image.

Step 812, positioning the eyebrow and eye areas in the face image.

Step 814, roughly positioning the upper eyelid line in the eye area.

Step 816, denoising the upper eyelid line.

Step 818, fitting the upper eyelid line.

Step 820, determining the eye state according to the shape of the upper eyelid line (e.g. the curvature or curvature feature value). Taking the quadratic coefficient a of the polynomial obtained by fitting as a basis of determination. Determining the upper and lower thresholds Ch and Cl, with the lower threshold Cl guaranteeing that the determination of eye closure will not be wrong in most cases. For guaranteeing the adaptability, the lower threshold Cl can also be not alone as a basis of determination. In Step 822, if the quadratic coefficient a is higher than the upper threshold Ch, the eyes are thought to be opened; if the quadratic coefficient a is lower than the lower threshold Cl, the eyes are thought to be closed, and then Step 830 is executed, otherwise goes to Step 824.

Figure 9:
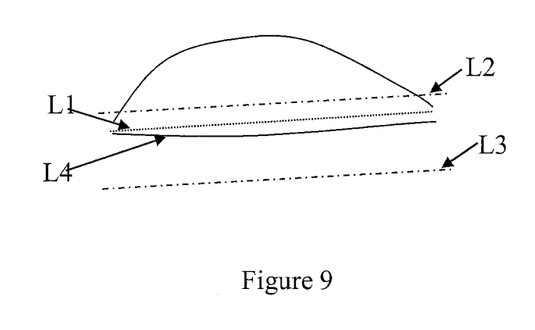
FIG. 9 is a schematic view of positioning the lower eyelid line.

Step 824, when the quadratic coefficient a is between the first and second thresholds, an auxiliary determination is performed on the eye state. Detecting the lower eyelid line according to the detected upper eyelid line, taking a certain range above or below the line connecting the left and right points of the eyelid line after fitting as the scanning area of the lower eyelid line, such as a certain range above or below the dotted line L1 as shown in FIG. 9 (e.g. the area between the dotted lines L2 and L3 in FIG. 9), and acquiring the lower eyelid line by scanning with the rectangular feature template, such as the line L4 in FIG. 9.

The lower eyelid line can also be obtained by matching many times from roughness to preciseness in the way obtaining the upper eyelid line.

Step 826, computing the average spacing between the upper and lower eyelid lines.

Step 828, determining whether the eyes are closed according to the average spacing between the upper and lower eyelid lines. Using the average spacing between the upper and lower eyelids as a second basis of determination, determining two reference thresholds, one reference threshold Dl being greater and tending to guarantee that the closed eyes will not be erroneously determined as opened eyes, the other reference threshold Ds being smaller and tending to guarantee that the opened eyes will not be erroneously determined as closed eyes. According to the position of the quadratic coefficient a between the upper and lower thresholds as shown by the formula $Dd=Dl-(Dl-Ds)*((a-Cl)/(Ch-Cl))$, taking the sliding of the spacing threshold Dd between the reference thresholds as a basis of determination; the spacing threshold slides toward Ds when the quadratic coefficient a is close to Ch, and vice versa. When the average spacing between the upper and lower eyelids is greater than the spacing threshold, the driver's eyes are determined to be opened, otherwise to be closed. Execute Step 830 according to the determination results.

Step 830, collecting statistics on the historical data of the eye closure state, and comparing the statistical results with a preset conditions, thus determining whether the driver is in a fatigue state.

In this example, the lower eyelid line can also be detected after the upper eyelid line is fitted, i.e. based on the processed upper eyelid line.

This example uses the average spacing between the upper and lower eyelids for an auxiliary determination; for the cases that the first determining module cannot determine, a final determination is made with a variable threshold according to the radian of the upper eyelid. The average spacing between the upper and lower eyelids is stable for determining that the eyes are closed, while the radian of the upper eyelid is stable for determining that the eyes are opened, the combination of both increasing the adaptability of the fatigue-driving determining algorithm The above modules or processes can be compiled into a program, which can be installed in a computer including various processors.

The program compiled from the above modules or processes can be stored in an external readable storage medium, which can be a floppy disk, a CD-ROM, a hard disk, a tape recording medium, a semiconductor memory of the IC card, or other optical recording media (e.g. DVD or PD) or magnetic recording media. The media further include electrical, optical, acoustic or other forms of communication signals (e.g. carrier waves, infrared signals, and digital signals).

The above examples can be applied on an automobile for detecting whether the driver is in a fatigue driving state; in an example, the automobile includes a camera device and the fatigue-driving detecting device of any of the above examples. The camera device is fixed near the driver's position for taking the driver's face image, such as the image of the driver's entire face or the image of driver's upper half face. The camera device can be an infrared camera or other types of camera. The camera device outputs the driver's face image data to the fatigue-driving detecting device, which determines whether the driver is in the fatigue driving state after processing the image data by the way as described in the above-mentioned examples.

In another example, the automobile further includes an alarm device to which the fatigue-driving detecting device is coupled; when the driver is in the fatigue driving state, the fatigue-driving detecting device outputs an alarm signal to the alarm device, controlling the alarm device to give a sound and/or light alarm.

What is described above is the further detailed explanation of the present application in combination with the specific embodiments; however, it cannot be considered that the specific embodiments of the present application are only limited to the explanation. For those of ordinary skill in the art, some simple deductions or replacements can also be made under the premise of the concept of the present application, and shall be all regarded as within the scope of protection of the present application.

What is claimed is:

1. A method for detecting fatigue driving, comprising:
analyzing a driver's eye image with a rectangular feature template to obtain an upper eyelid line, in particular, traversing the eye image by columns with the rectangular feature template and recording a location in each column where the feature value of the rectangular feature template is maximal, the feature value of the rectangular feature template referring to a greyscale difference between upper and lower halves of a rectangle where the rectangular feature template is located, and obtaining the upper eyelid line by taking the central point of the rectangular feature template at the location as a point on the upper eyelid line;
determining the eye closure state according to a curvature or curvature feature value of the upper eyelid line; and
collecting statistics on the eye closure state and thereby determining whether the driver is in a fatigue state.

2. The method according to claim 1 wherein before traversing the eye image with the rectangular feature template, integrating the eye image to obtain an integral eye image; and the step of traversing the eye image with the rectangular feature template comprises: traversing the integral eye image with the rectangular feature template, computing the feature value of the rectangular feature template at each location.

3. The method according to claim 1, wherein multiple scanning the eye image with rectangular feature templates of sizes from big to small to obtain the upper eyelid line; and the size of the rectangular feature templates is determined dynamically according to the size of the eye image.

4. The method according to claim 1, further comprising: denoising the upper eyelid line after obtaining the upper eyelid line and before determining the eye closure state according to the curvature of the upper eyelid line.

5. The method according to claim 4, wherein the step of denoising comprises:
  detecting discontinuous points on the eyelid line, and dividing the eyelid line into several sections by taking the abruptly-changed point as segmentation points;
  determining a trust section on the eyelid line as a basis of the eyelid line; and
  scanning locally with the rectangular feature template from both ends of the trust section respectively toward both sides to obtain a corrected eyelid line.

6. The method according to claim 1, wherein after obtaining the upper eyelid line, further comprising: performing curve fitting on the eyelid line with a quadratic polynomial to get a quadratic polynomial expression of the eyelid line, regarding a quadratic coefficient of the quadratic polynomial expression as the curvature or curvature feature value of the upper eyelid line; the step of determining the eye closure state according to the curvature or curvature feature value of the upper eyelid line comprises:
  comparing the quadratic coefficient with a preset eyelid-line curvature threshold; and
  thereby determining whether the driver's eyes are opened or closed.

7. The method according to claim 6, wherein the eyelid-line curvature threshold includes a first threshold and a second threshold less than the second threshold; when the quadratic coefficient is greater than the first threshold, the driver's eyes are determined to be opened; when the quadratic coefficient is less than the second threshold, the driver's eyes are determined to be closed; when the quadratic coefficient is between the first and second thresholds, an auxiliary determination of the eye closure state is further performed according to a spacing between the upper and lower eyelids.

8. The method according to claim 7, wherein the auxiliary determination of the eye closure state according to the spacing between the upper and lower eyelids comprises:
  scanning the eye image with the rectangular feature template based on the acquired upper eyelid line to obtain the lower eyelid line;
  computing an average spacing between the upper and lower eyelid lines; and
  comparing the average spacing between the upper and lower eyelid lines with a preset eyelid-line spacing threshold, and thereby determining whether the driver's eyes are opened or closed.

9. The method according to claim 1, wherein the step of collecting statistics on the eye closure state and thereby determining whether the driver is in a fatigue state comprises:
  collecting statistics on a duration when the eyes are closed in a recent time, and determining that the driver is in a fatigue state if the eye closed duration exceeds a specified duration; or
  collecting statistics on a time ratio of eye open duration to eye closed duration in unit time, and determining that the driver is in a fatigue state if the time ratio exceeds a certain threshold.

10. A fatigue-driving detecting device, comprising:
  an upper-eyelid-line acquiring module for scanning a driver's eye image with a rectangular feature template to obtain an upper eyelid line, comprising:
  a scanning unit for sliding the rectangular feature template on each column of the eye image;
  a greyscale-difference calculating unit for recording the location in each column where the feature value of the rectangular characteristic template is maximal, the feature value of the rectangular feature template referring to the greyscale difference between the upper and lower halves of the rectangle where the rectangular feature template is located;
  an upper-eyelid-line plotting unit for obtaining the upper eyelid line by taking the central point of the rectangular feature template at the location as a point on the upper eyelid line;
  a first determining module for determining the eye closure state according to a curvature or curvature feature value of the upper eyelid line; and
  a fatigue-state determining module for collecting statistics on the eye closure state and thereby determining whether the driver is in a fatigue state.

11. The device according to claim 10, wherein the upper-eyelid-line acquiring module further comprises an integrating unit used for integrating the eye image before traversing the eye image to obtain the integral eye image; the upper-eyelid-line acquiring module is configured for scanning the integral eye image with the rectangular feature template, computing the feature value of the rectangular feature template at each location.

12. The device according to claim 10, further comprising: a denoising module used for denoising the obtained upper eyelid line, comprising:
  an eyelid-line dividing unit for detecting discontinuous points on the eyelid line, and dividing the eyelid line into several sections by taking the discontinuous points as segmentation points;
  a trust-section determining unit for determining a trust section on the eyelid line as a basis of the eyelid line; and
  an eyelid-line correcting unit for scanning with the rectangular feature template from both ends of the trust section respectively toward both sides to obtain a corrected eyelid line.

13. The device according to claim 10, further comprising a fitting module used for performing curve fitting on the eyelid line with a quadratic polynomial to get a quadratic polynomial expression of the eyelid line, regarding a quadratic coefficient of the quadratic polynomial expression as the curvature or curvature feature value of the upper eyelid line; the first determining module is used for comparing the quadratic coefficient with a preset eyelid-line curvature threshold and thereby determining whether the driver's eyes are opened or closed.

14. The device according to claim 13, wherein the eyelid-line curvature threshold includes a first threshold and a second threshold less than the second threshold; when the quadratic coefficient is greater than the first threshold, the driver's eyes are determined by the first determining module to be in an opened state; when the quadratic coefficient is less than the second threshold, the driver's eyes are determined to be in a closed state; when the quadratic coefficient is between the first and second thresholds, a second determining module is further included for an auxiliary determination of the eye closure state according to a spacing between the upper and lower eyelids.

15. The device according to claim 14, further comprising:
a lower-eyelid-line acquiring module for scanning the eye image with the rectangular feature template based on the acquired upper eyelid line to obtain the lower eyelid line; the second determining module comprises:
an upper-and-lower eyelid line spacing computing unit for computing the average spacing between the upper and lower eyelid lines; and
a spacing comparing unit for comparing the average spacing between the upper and lower eyelid lines with the preset eyelid-line spacing threshold and thereby determining whether the driver's eyes are opened or closed.

16. The device according to claim 15, wherein the eyelid-line spacing threshold changes dynamically with the curvature or curvature feature value of the upper eyelid line; when the average spacing between the upper and lower eyelid lines is greater than the eyelid-line spacing threshold, the driver's eyes are determined to be in an opened state, otherwise to be in a closed state.

17. An automobile, comprising:
a camera device, fixed near the driver's position for taking the driver's face image; and
the fatigue-driving detecting device according to claim 10, arranged on the automobile for receiving and processing image data from the camera device.

18. A computer executable program stored on non-transitory magnetic or optical recording media can perform the following functions by a computer:
analyzing a driver's eye image with a rectangular feature template to obtain an upper eyelid line, in particular, traversing the eye image by columns with the rectangular feature template and recording the location in each column where the feature value of the rectangular characteristic template is maximal, the feature value of the rectangular feature template referring to a greyscale difference between the upper and lower halves of the rectangle where the rectangular feature template is located, and obtaining the upper eyelid line by taking the central point of the rectangular feature template at the location as a point on the upper eyelid line;
determining the eye closure state according to a curvature or curvature feature value of the upper eyelid line; and
collecting statistics on the eye closure state and thereby determining whether the driver is in a fatigue state.

19. The program according to claim 18, where the program can further perform the following functions by a computer:
after obtaining the upper eyelid line, performing curve fitting on the eyelid line with a quadratic polynomial to get a quadratic polynomial expression of the eyelid line, regarding a quadratic coefficient of the quadratic polynomial expression as the curvature or curvature feature value of the upper eyelid line; the step of determining the eye closure state according to the curvature or curvature feature value of the upper eyelid line comprises:
comparing the quadratic coefficient with a preset eyelid-line curvature threshold; and
thereby determining whether the driver's eyes are opened or closed.

20. A computer readable medium stored on non-transitory magnetic or optical recording media with a computer executable program, wherein the program can perform the following functions by a computer:
analyzing a driver's eye image with a rectangular feature template to obtain an upper eyelid line, in particular, traversing the eye image by columns with the rectangular feature template and recording the location in each column where the feature value of the rectangular feature template is maximal, the feature value of the rectangular feature template referring to a greyscale difference between the upper and lower halves of the rectangle where the rectangular feature template is located, and obtaining the upper eyelid line by taking the central point of the rectangular feature template at the location as a point on the upper eyelid line;
determining the eye closure state according to a curvature or curvature feature value of the upper eyelid line; and
collecting statistics on the eye closure state and thereby determining whether the driver is in a fatigue state.

* * * * *